United States Patent [19]

Kao et al.

[11] Patent Number: 4,835,101

[45] Date of Patent: May 30, 1989

[54] LUMINESCENT ANALYSES WITH ENHANCED STORAGE STABILITY

[75] Inventors: Richard Kao, Minnetonka; Frank A. Blocki, Chaska; Robert A. Pranis, Chaska; Walter C. Mahoney, Woodbury, all of Minn.

[73] Assignee: Kallestad Diagnostics, Inc., New York, N.Y.

[21] Appl. No.: 923,564

[22] Filed: Oct. 27, 1986

Related U.S. Application Data

[63] Continuation-in-part of Ser. No. 827,448, Feb. 10, 1986, abandoned.

[51] Int. Cl.$^4$ .......................... C12Q 1/00; C12Q 1/26; G01N 21/76
[52] U.S. Cl. ........................................ 435/28; 435/4; 435/25; 435/810; 436/172; 436/808; 436/826
[58] Field of Search ................. 435/4, 7, 28; 436/826, 436/172

[56] References Cited

U.S. PATENT DOCUMENTS 4,483,929 11/1984 Szoka ........................................ 435/7
4,598,044 7/1986 Kricka et al. .......................... 435/28

OTHER PUBLICATIONS

Phenols as Enhancers of the Chemiluminsecent Horseradish Peroxidase-Luminol-Hydrogen Peroxide Reaction: Application in Luminescence-Monitored Enzyme Immunoassays, Clin. Chem. 31:1335-1341 (1985), Thorpe, et al.
Luminescent Immunoassays: New Labels for an Established Technique, Kricka, et al, Diagnostic Medicine, May, 1984, pp. 45-52.
A Rapid Luminescently Monitored Enzyme Immunoassay for IgE, J. Immunol. Methods 79:57-63 (1985), Thorpe, et al.
Enhanced Luminescence Determination of Horseradish per Oxidase Conjugates, Anal. Chem. Acta 170:101-107 (1985), Thorpe, et al.
An Immunoassay for Serum Thyroxine Employing Enhanced Luminescent Quantitation of Horseradish Peroxidase Conjugates, Thorpe, et al, Anal. Applications of Bioluminescence and Chemiluminescence, Krica, Ed, Academic Press, London, 1984, pp. 243-248.
Enhanced Luminescence Enzyme Immunoassay for Factor VIII Related Antigen, J. Clin. Pathol. 38:317-319 (1985), Wang, et al.
Enhanced Luminescence Procedure for Sensitive of Peroxidase-Labeled Conjugates in Immunoassay, Nature 305:158-159 (1983).
Enhancement of the Horseradish Peroxidase-Catalyzed Chemiluminescent Oxidation of Cyclic Diacyl Hydrazides by 6-Hydrobenzothiazoles, Anal. Biochemistry, 145:96-100 (1985), Thorpe, et al.
Photographic Monitoring of Enhanced Luminescent Immunoassays, Clin. Chem. 30:806-807, Thorpe, et al.
An Enhanced Luminescence Dot-Immunobinding Assay for Cytomegalovirus Antibody Monitored Using Instant Photographic Film, Anal. Letters 18:1307-1320 (1985), Sampson, et al.

(List continued on next page.)

Primary Examiner—Robert J. Warden
Assistant Examiner—Janelle Graeter
Attorney, Agent, or Firm—James R. Haller

[57] ABSTRACT

The storage stability of peroxidase-reactive luminescent cocktails which employ chemiluminescent 2,3-dihydro-1,4-phthalazinediones, oxidants reactant therewith to cause light emission in peroxidase-mediated luminescent reactions, and phenolic sensitivity enhancers is improved by maintaining the pH of the cocktail prior to use at a value in the range of about 3 to about 6 and preferably at a pH of about 5. An analyte sample may be subjected to a reaction resulting in a peroxidase-containing phase, the peroxidase content of which is related to the quantity of analyte in the sample, and the peroxidase phase may then be combined with the thus-described cocktail and an aqueous alkaline organic buffer to raise the pH of the resulting reaction mixture to a value in the range of 7-9, favoring light emission.

25 Claims, 2 Drawing Sheets

OTHER PUBLICATIONS

Enhanced Luminescent Enzyme Immunoassays for Rubella Antibody, Immunoglobulin E and Digoxin, Biochemical and Biophysical Research Communications 119:481–487 (1984), Thorpe, et al.

Applications of Enhanced Quantitation of Horseradish Peroxidase (HRP) Labels in Immunoassays, Clin. Chem. 31:913 (1985) (Abstract), Thorpe, et al.

Camera Luminometer for use with Luminescent Assays, Analyst 110:657–663 (1985), Bunce, et al.

Investigation ofo a Novel Solid Phase Chemiluminescent Analytical System, Incorporating Photographic Detection, for the Measurement of Glucose, Talanta 29:529–531 (1982), Carter, et al.

STABILITY AT 37° C

BUFFER-MEDIATED LUMINESCENCE

THYROXINE (T$_4$) ASSAY

LUMINESCENT ANALYSES WITH ENHANCED STORAGE STABILITY

This application is a continuation-in-part of application Ser. No. 06/827,448, filed Feb. 10, 1986, now abandoned.

FIELD OF THE INVENTION

This invention relates to luminescent assays and to reagents, methods and kits useful in the performance of such assays.

BACKGROUND OF THE INVENTION

Of the assays which are widely used for determining the presence and quantity of various biological molecules, drugs and the like, radioimmunoassays have been preferred for reasons of sensitivity, accuracy and precision. Because radioimmunoassays employ radioactive isotopes such as iodine-125, many researchers have turned to non-radioactive immunoassays to avoid the need for handling and disposing of radioactive materials and to avoid also the necessity of dealing with a complicated licensing and reporting structure.

Recent technologies have involved the use of immunological assays that employ a reporter molecule that is not radioactive. Of these, luminescent assays are quite comparable to radioimmunoassays in terms of sensitivity, accuracy and precision, and can be extremely fast. One such luminescent assay is described in European Patent Application No. 84300725.3, published Aug. 22, 1984 as Publication No. 116,454 and entitled ENHANCED LUMINESCENT OR LUMINOMETRIC ASSAY, the inventors of which are listed as T. Whitehead, L. Kricka and G. Thorpe. This application describes the use of peroxidase-based conjugates as a tracer system, light being emitted when the peroxidase conjugate is combined with a chemical "cocktail" containing, e.g., luminol as a chemiluminescent reactant, an enhancer compound such as p-iodophenol and an oxidant such as $H_2O_2$.

In addition to the European Patent Application described above, reference is made to the following:

Thorpe, G. H. G., Kricka, L. J., Mosely, S. B., and Whitehead, T. B., *Phenols As Enhancers Of The Chemiluminescent Horseradish peroxidase-Luminol-Hydrogen Peroxide Reaction: Application in Luminescence-monitored Enzyme Immunoassays,* Clin. Chem. 31: 8, 1335–1341 (1985).

Kricka, L. J., and Whitehead T. P. *Luminescent Immunoassays: New Labels For An Established Technique.* Diagnostic Medicine, May, 1984; pp. 45–52.

Wang, H., George, J., Thorpe, G. H. G., Stott R. A., Kricka, L. J., and Whitehead T. P. *Enhanced Luminescence Enzyme Immunoassay For Factor VIII Related Antigen.* J. Clin. Pathol. 1985; 38: 317–319.

Thorpe, G. H. G., Williams, L. A., Kricka, L. J., Whitehead, T. P., Evans, H. and Stanworth, D. R. (1985) *A Rapid Luminescently Monitored Enzyme Immunoassay For IgE.* J. Immuno. Methods 79: 57–63 (1985).

Thorpe, G. H. G., Mose, S. B. Kricka. L. J., Stott, R. A. and Whitehead, T. P. *Enhanced Luminescence Determination of Horseradish Peroxidase Conjugates.* Anal. Chim. Acta 170: 101–107 (1985).

Whitehead, T. P., Thorpe, G. H. G., Carter, T. J. N., Groucutt, C., and Kricka L. J. *Enhanced Luminescence Procedure for Sensitive Determination of Peroxidase-Labelled Conjugates in Immunoassay.* Nature 305: 158–159 (1983).

Thorpe, G. H. G., Kricka, L. J., Gillespie, E., Moseley, S., Amess, R., Baggett N. and Whitehead, T. P. *Enhancement of the Horseradish Peroxidase- catalyzed Chemiluminescent Oxidation Of Cyclic Diacyl Hydrazides by 6-Hydroxybenzothiazoles.* Analytical Biochemistry 145: 96–100 (1985).

Sampson, I., Mattews, J. A., Thorpe, G. H. G., and Kricka, L. J. *An Enhanced Luminescence Dot-immunobinding Assay For Cytomegalovirus Antibody Monitored Using Instant Photographic Film.* Analytical Letters 18: 1307–1320 (1985).

Thorpe, G. H. G., Haggart, R., Kricka, L. J., and Whitehead, T. P. *Enhanced Luminescent Enzyme Immunoassays For Rubella Antibody, Immunoglobulin E and Digoxin.* Biochemical and Biophysical Research Communications 119: 481–487 (1984).

A major problem with luminescent assays has been a lack of stability of certain of the luminescent reactants. An additional problem has involved the interference of the luminescent reaction caused by the analyte sample itself. Together, these problems appear to have contributed to the lack of commercialization of immunological tests which employ a luminescent reporter system. We have found that a major drawback with the enhanced luminescent or luminometric assay, referred to above, is the lack of stability of the so-called luminescent "cocktail", a combination of reactants. In addition, we have found that the ability of such cocktails to enter into the light-emitting reaction is severely reduced when the cocktails are maintained at room temperature for more than a few days or are maintained at 37° C. for as short as one day. Thus, such reagent "cocktails" could not withstand elevated temperatures often encountered in normal commercial shipping procedures. Since light is emitted when this cocktail is combined with a peroxidase conjugate, cocktail instability is a serious drawback and limits the usefulness of an otherwise valuable technology.

Additionally, we have found that under certain circumstances, buffer-mediated luminescence, that is, luminescence not caused or "mediated" by peroxidase, can be a significant problem, particularly when high sensitivity is required. Reagents such as the buffers and cocktails described above should desirably have no intrinsic luminescent properties, i.e., they should not emit light other than as a consequence of a peroxidase mediated luminescent reaction.

SUMMARY OF THE INVENTION

We have found that the storage stability of luminescent "cocktails" which contain peroxidase-reactive chemiluminescent reactants, oxidants and sensitivity enhancing materials can be greatly improved through the use of a pH-regulating composition which regulates the pH of the cocktail to a value in the range of about 3 to about 6, instead of the usual pH of 8.5 which is the approximate pH at which maximum light emission occurs from a chemiluminescent reaction of the type described. Stability appears to be maximized at a pH of about 5.0. Thus, the invention in one embodiment relates to a reagent (a "cocktail") that is useful in luminescence-monitored enzyme assays and which is capable, when reacted with peroxidase, of undergoing a luminescent, that is, light-emitting, reaction. The reagent comprises a chemiluminescent compound (preferably a 2,3-dihydro-1,4-phthalazinedione) and an oxidant reactive therewith to cause light emission in a peroxidase-mediated luminescent reaction, and a sensitivity enhancer (preferably phenolic) capable of increasing the signal-to-background ratio of said luminescent reaction. The reagent is characterized by including a pH-regulating composition regulating the pH of the reagent to a value in the range of about 3 to about 6, and preferably at about 5.0. The phthalazinedione chemiluminescent reagent preferably is luminol or isoluminol, the oxidant preferably is hydrogen peroxide, perborate ion or urea peroxide, and the sensitivity enhancer preferably is a substituted phenol such as 4-iodophenol or 4-phenylphenol.

In another embodiment, the invention relates to a method of increasing the storage stability of a reagent containing the above-described chemiluminescent compound, an oxidant, and luminescent enhancing reactant, the method comprising controlling, during storage, the pH of the reagent to a value in the range of about 3 to about 6, and preferably about 5.0.

In yet another embodiment, the invention relates to an assay kit for performing a luminescence-monitored enzyme assay such as an immunoassay for an analyte. The kit comprises a vessel containing a reagent that includes the peroxidase-mediated chemiluminescent compound, an oxidant, and the sensitivity enhancing reactant referred to above in an aqueous solution buffered to a pH in the range of about 3 to about 6 (preferably at about 5.0), and a separate vessel containing an alkaline aqueous buffer solution compatible with the luminescent reaction to adjust the pH of the luminescent reaction mixture containing the first reagent to a value favoring light emission, such as approximately pH 8.5.

In yet another embodiment, the invention relates to a method for performing an assay for an analyte in an analyte sample which comprises subjecting the analyte to a reaction that results in a peroxidase-containing phase, the quantity of peroxidase in which is related to the quantity of analyte in said sample, and combining said peroxidase phase with a first reagent comprising a chemiluminescent 2,3-dihydro-1,4-phthalazinedione, an oxidant reactive therewith to cause light emission in a luminescent reaction and a phenolic sensitivity enhancer capable of increasing the signal to noise ratio of the luminescent reaction, the reagent having a pH in the range of about 3 to about 6 (and preferably about 5.0), and a buffer solution of appropriate quantity and pH to provide the resulting reaction mixture with an alkaline pH favoring light emission therefrom.

We have also found that background or "noise" luminescence in certain luminescent reactions is caused by the alkaline, organic buffer utilized to stabilize the pH of the reaction mixture at a value favoring light emission. The luminescence caused or "mediated" by certain buffers - particularly "Tris" (($HOCH_2)_3CNH_2$) decays slowly, but luminescence due to other buffers, such as Tricine (($HOCH_2)_3 CNHCH_2COOH$) and glycylglycine ($H_2NCH_2 CONHCH_2COOH$) decays quickly to negligible levels within about five minutes and usually within about three minutes. Hence, the invention in a further embodiment relates to the use of an alkaline, organic buffer which, when combined with the "cocktail" referred to above, does not emit more than a negligible amount of light after about two to three minutes.

It has also been found that the peroxidase-mediated luminescent output, but not background luminescence, can be significantly increased by carrying out the luminescence reaction in the presence of calcium chloride in a given concentration range. Hence, another embodiment of the invention resides in the use of predetermined amounts of $CaCl_2$ in the luminescence reaction, the $CaCl_2$ being contained desirably in the alkaline buffer.

DESCRIPTION OF THE PREFERRED EMBODIMENT

Figure 1:
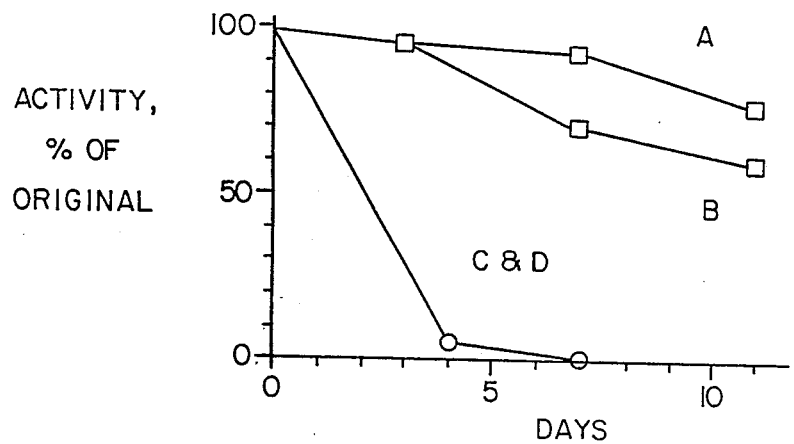
FIG. 1 is a grap in which the activity of various luminescent cocktails is plotted against storage time at 37° C.

The invention is particularly adapted for use in assays utilizing specific binding pairs. The specific binding partners may be, for example, antibodies and antigens, specific bio-molecule pairs such as avidin-biotin, hormones and hormone receptors, enzymes and their specific binding partners such as cofactors and inhibitors, and the like.

The basic chemiluminescent "cocktail" reagent used herein is reactive with peroxidase to emit light, the intensity of which is related to the amount of peroxidase thus reacted. The reagent is particularly characterized by being maintained, during storage, at a pH of from about 3 to about 6, and preferably at about 5.0. The luminescent reaction is carried out at an alkaline pH, generally in the range of about 7.0 to about 9.0 and, desirably, at about pH 8.5.

The peroxidase is derived from subjecting an analyte sample to a reaction that results in a peroxidase-containing phase, the quantity of peroxidase in which is related to the quantity of analyte in the sample. For example, a sample of an analyte, typically a member of a specific binding pair and usually an antigen, may be combined with a known quantity of an analyte-peroxidase conjugate or the peroxidase conjugate of an analyte binding partner and with the other member of the specific binding pair, usually an antibody, bound to a solid substrate such as glass beads, etc. After a short incubation period, during which the analyte and the analyte-peroxidase conjugate or the binding partner conjugate compete for binding sites on the binding partner or analyte, respectively, the solid and liquid phases may be separated. It will be understood that the amount of peroxidase conjugate bound to the solid phase will relate quantitatively to the amount of analyte in the sample. Conversely, the amount of peroxidase conjugate in the liquid phase may similarly relate quantitatively to the amount of analyte in the sample. The general protocols involving immunoassays and other assays involving specific binding partners are well known, and further explanation is unnecessary.

In one exemplary method, an analyte sample and an analyte-horseradish peroxidase (HRP) conjugate are combined in a transparent cuvette containing, bound to beads or other solid surface, an antibody to the analyte. After a short incubation period, the liquid phase is separated and discarded and the reagent "cocktail" at pH 3-6 and sufficient buffer to raise the pH of the resulting system to a value favoring light emission, e.g., about 8.5, are added to the cuvette. Light emission occurs rapidly, usually in a matter of seconds. Once any buffer mediated luminescence has decayed to a negligible level (commonly taking less than three minutes), the luminescence emanating from the cuvette is measured, e.g.. by means of a luminometer, and the resulting value is related to the quantity of analyte in the sample.

In another exemplary method, an analyte sample and an HRP-conjugated antibody to the analyte are combined in a reaction vessel containing, bound to a solid substrate such as the vessel walls, a second antibody to the analyte. After a short incubation period, the liquid and solid phases are separated, the "cocktail" and alkaline buffer are added to the vessel, and the light emitted in the resulting peroxidase-mediated luminescent reaction is measured and is related quantitatively to the amount of analyte in the sample.

The luminescent reagent comprises a 2,3-dihydro-1,4-phthalazinedione as a chemiluminescent material. an oxidant reactive therewith to cause light emission in a peroxidase-mediated chemiluminescent reaction, and a phenolic sensitivity enhancer capable of increasing the amount of light emitted due to the peroxidase-mediated reaction—that is—of increasing the signal-to-background ratio of light emission. The ingredients thus identified have been fully described and characterized in the references listed above, and the invention is not dependent upon the precise selection among the thus described cocktail reagents. The 2,3-dihydro-1,4-phthalazinedione chemiluminescent reactant desirably is luminol or isoluminol, although other phthalazinedione chemiluminescent compounds (that is, compounds that are converted to excited states in a chemiluminescent reaction and then return to non-excited states with emission of photons) also are applicable. Chemiluminescent compounds useful in the present invention thus are those which will react with a peroxidase to emit light. A candidate chemiluminescent compound may be tested as follows:

Diluted horseradish peroxidase (0.5 ng)(100 $\mu$l) in Tricine-HCl pH 8.5 buffer is placed in each of three transparent cuvettes containing the candidate chemiluminescent compound at three different concentrations (containing, respectively, 5, 10 and 20 $\mu$l of a solution of 1 mg/ml in the Tricine-HCl buffer). Each cuvette is then placed in a luminometer ("Piclight 6500", Packard Instrument Company, as an example). $H_2O_2$ (100 $\mu$l of a 0.3% aqueous solution) is then added and the light output is measured. Levels of light output are compared with negative controls (containing no chemiluminescent materials). Appropriate chemiluminescent compounds should show significant light output at each of the three concentrations.

The oxidant may be any oxidant that reacts with the chemiluminescent compound to cause light emission in a chemiluminescent reaction. A simple selection technique involves the use of the test method set out above, utilizing luminol as the chemiluminescent compound and substituting a candidate oxidant for the $H_2O_2$. Preferred oxidants are $H_2O_2$, perborate ion and urea peroxide. Of these, urea peroxide is preferred.

The phenolic sensitivity enhancer, preferably a substituted phenol such as 4-iodophenol or 4-phenylphenol, is capable of increasing the amount of light that is generated in the peroxidase-mediated luminescent reaction. A simple selection test for appropriate phenolic enhancers is as follows:

Diluted horseradish peroxidase (0.5 ng) in Tricine-HCl pH 8.5 buffer is placed in each of three cuvettes. Three different concentrations of the candidate enhancer (5, 10 and 20 $\mu$l; 1 mg/ml in the Tricine buffer) are added, respectively, to the three cuvettes, and each is placed in a luminometer. To each cuvette is then added 300 $\mu$l of a solution of luminol (60$\mu$M) and $H_2O_2$ (2.1 mM). The level of light that is emitted from each cuvette is compared with a control in which the candidate enhancer was replaced with Tricine buffer. The enhancers useful in the invention cause substantial amplification of the light output.

The buffer that is employed to adjust the pH of the luminescent reaction mixture to an alkaline value favoring ight production should itself contribute only negligibly if at all to the amount of luminescence that is detected after a short period of time. Buffers that are useful in the invention desirably exhibit pKa's in the range of about 7.0-9.5 and, when mixed with a "cocktail" such as that described below in Example I, should produce negligible, if any, luminescence. "Negligible buffer-mediated luminescence," as used herein, means that buffer-mediated luminescence, measured three minutes from the start of the luminescent reaction, is not greater than about 500 times the background luminescence, all as measured on a single photon counting instrument. The test may be run as follows:

A candidate buffer is prepared as a 100 mM aqueous soution at pH 8.5, 100 $\mu$l of the candidate buffer is injected into a transparent cuvette, followed by 100 $\mu$l of the luminescent reagent "cocktail" described below in Example I. Luminescent output is measured by a single photon counting instrument such as the "Lumac Biocounter", Model 2010, a product of 3M Company, the resulting counts being labeled "buffer-mediated" counts. The same experiment is repeated, replacing the candidate buffer with 100 $\mu$l of deionized water, the counts measured after three minutes being referred to as "background" counts. The ratio of buffer-mediated counts to background counts should not exceed about 500/1 and preferably should not exceed 100/1. In one experiment, using the "Lumac Biocounter" instrument referred to above, "background counts" of seven were measured. A Tricene buffer provided "buffer-mediated" counts of 364, yielding a ratio of about 52/1. A "Tris" buffer provided "buffer-mediated" counts of 4907 yielding a ratio of about 700/1. A glycyglycine buffer provided "buffer-mediated" counts of 160, yielding a ratio of about 23/1.

Of importance, the luminescent reagent, (the "cocktail") is maintained at a pH in the range of from about 3 to about 6, and preferably at about 5, through the use of an appropriate buffer such as an acetate or citrate buffer until it is to be used.

The luminescent compounds, the oxidants and the enhancer reactants are discussed more fully in the European Patent Office Publication No. 116,454 identified above, the teachings of which are incorporated herein by reference.

It has further been found that the luminescent output, but not the background luminescence, can be significantly increased by carrying out the luminescent reaction in the presence of calcium chloride in a given concentration range. In general, substantial enhancement of the peroxidase-mediated light output is observed at low concentrations of calcium ion without substantial increases in background light output. However, higher calcium ion concentrations result in significant increases in background luminescence without proportional increases in peroxidase-mediated luminescence. Accordingly, it is desired to use calcium ion concentrations sufficient to substantially enhance peroxidase-mediated light output but not background light output. Calcium chloride is the preferred calcium ion source. The concentration range of calcium chloride to be used for enhancement of the light output of any peroxidase-mediated luminescent reaction can readily be experimentally determined.

Although calcium chloride can be included as an ingredient of the "cocktail" or can be added to the luminescent reaction mixture, the calcium chloride preferably is contained in a desired concentration in the alkaline buffer.

EXAMPLE I

A luminescent reagent ("cocktail") was prepared from the following stock solutions:
 (a) Purified luminol is dissolved in dimethyl sulfoxide (DMSO) at a concentration of 10 mg/ml.
 (b) Recrystallized 4-iodophenol is dissolved in DMSO at a concentration of 88 mg/mL.
 (c) A 25 mM acetate pH 5.0 buffer solution is produced by mixing a 25 mM sodium acetate solution with a 25 mM glacial acetic acid solution until a pH of 5.0 is reached. Acetate and citrate buffers as used herein are commonly known and commonly comprise mixtures of the acids and alkali metal salts in aqueous solutions. For example, a citrate buffer stock solution may be produced simply by using citric acid and sodium citrate in the proportions used above.
 (d) Urea peroxide is dissolved in the acetate buffer stock solution at a concentration of 10 mg/ml.

To 98 ml of the acetate buffer stock solution (c) is added 106.3 $\mu$l of the luminol stock solution (a), 90.0 $\mu$l of the 4-iodophenol stock solution (b) and 2540.0 ul of the urea peroxide stock solution (d), the cocktail having a final pH of 5.0.

To an aliquot of the thus prepared cocktail was added sufficient 100 mg Tricine buffer to raise the pH of the cocktail to a value of 8.5, and HRP 0.25 ng was added to test for light production. The intensity of light emitted after approximately five minutes was recorded. Aliquots of the thus described cocktail were stored for a period of two weeks at a temperature of 37° C., and were periodically tested for light output by adding Tricene buffer and HRP, as set out above. Light output was reported as a percentage of the initial liqht output ("percentage activity"), and are reported as curve "A" in the graph of FIG. 1.

EXAMPLE II

The procedure of Example I was duplicated exactly except that the urea peroxide oxidant was replaced with sodium perborate (2.1 mM) ion. The results of storage at 37° are reported graphically as curve "B" in FIG. 1.

EXAMPLE III

Example II was repeated exactly, except that the pH of the cocktail before storage was adjusted to a value of 8.5 through the addition of 100 mM Tris buffer ((HOCH$_2$)$_3$CNH$_2$) , and light output (by adding HRP but not the Tricine buffer) was periodically measured and is reported graphically in FIG. 1 as curve "C". Compared to the cocktails of Examples I and II stored at a pH of 5.0, the cocktail of this Example III exhibited extremely poor stability.

EXAMPLE IV

The procedure of Example III was followed exactly except that the perborate oxidant was replaced with 1.1 mM hydrogen peroxide. As shown in FIG. 1 by curve "D", poor storage results, similar to those of Example III, were obtained.

EXAMPLE V

Aliquots of the cocktail prepared in Example I were also stored at 4° C. and at room temperature, and periodically were tested for light output in the manner described in Example I. After two weeks of storage, the aliquots at 4° C. and at room temperature exhibited light outputs greater than 90% of the initial light outputs.

EXAMPLE VI

The procedure of Example V was repeated exactly with the cocktail of Example II. Similar results were obtained.

EXAMPLE VII

The procedure of Example V was repeated with procedure reported in Example III. Although at least 90% of the original light-producing activity was retained after two weeks for the aliquots maintained at 4° C., less than 70% of light-producing activity was retained after seven days storage at room temperature.

EXAMPLE VIII

The procedure of Example VII was repeated exactly with respect to the cocktail described above in Example IV. Again, the aliquots stored at 4° C. retained at least 90% of their light-emitting activity after two weeks. The aliquots stored at room temperature maintained 90% activity for only one week.

EXAMPLE IX

Figure 2:
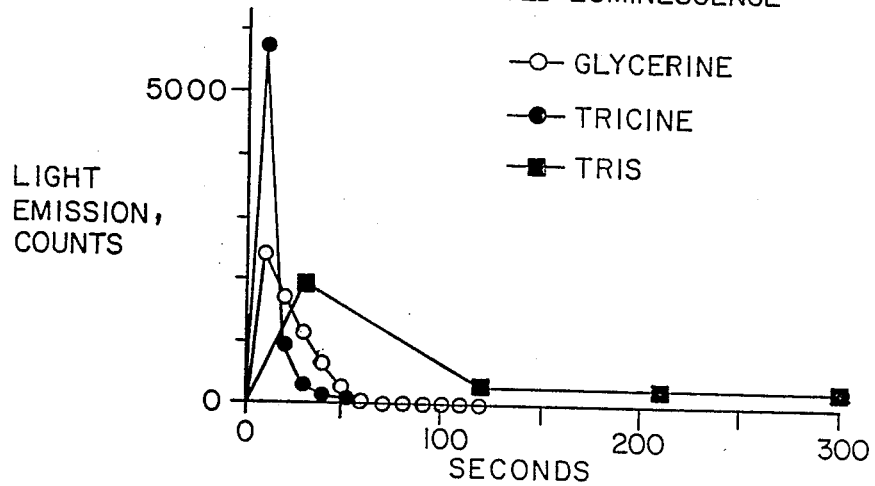
FIG. 2 is a graph in which luminescence resulting from several different buffers is plotted against time.

The procedure of Example I was followed exactly, except that the HRP component was omitted. Initial luminescence, due to the presence of the Tricine buffer, was observed but decayed to a negligible level within about 180 seconds. The same experiment was repeated using, in place of the Tricine buffer, (i) a 100 mM (pH 8.5) glycylglycine buffer and (ii) a Tris-HCL buffer. Each buffer was added in an amount sufficient to raise the pH of the reaction mixture to approximately 8.5. The initial luminescence due to the glycylglycine buffer decayed to a negligible level in about 180 seconds. The light emitted from the sample utilizing the Tris buffer, although decayed substantially within about two minutes, subsisted for a time period exceeding ten minutes at a low but significant level (700 × background count). The results are reported in graphical form in FIG. 2. It will be understood that the background "noise" resulting from the use of the Tris buffer will substantially reduce the signal-to-noise ratio of a luminescent assay, whereas the glycylglycine buffer and, particularly, the Tricine buffer, do not noticeably contribute to background noise. It will now also be understood that luminescent assays performed in accordance with the invention desirably measure the light output from a reaction mixture after sufficient time has elapsed to permit buffer-mediated luminescence to decay to negligible levels. Luminescence may be measured at a given time after the reactants have been mixed, or, desirably, luminescent output may be integrated over a period of time beginning after decay of background luminescence (if any) to a negligible level.

EXAMPLE X

Rotavirus Assay (a) Preparation of Antibody-coated Tubes:

Rabbit anti-rotavirus IgG diluted at 1:10,000 in 0.06M carbonate buffer at a pH of 9.8 was contacted with the interior of polystyrene tubes for a period of fourteen hours at 4° C. to immobilize the antibody on the tube walls. The tubes subsequently were washed five times in phosphate buffered saline (PBS, pH 7.4) containing 0.5 ml per liter of a detergent, Tween 20 (J. T. Baker Chemical Co.) ("PBS-Tween").

(b) Preparation of HRP-Conjugated Murine Monoclonal antibody:

1.0 ml of PBS is added to 1.0 ml of a commercially available murine monoclonal antibody to rotavirus (a product of Kallestad Laboratories division of Erbamont Inc.). To this mixture is added 2.0 ml of 40% $Na_2SO_4$, and the mixture is stirred gently for thirty minutes at room temperature and then is centrifuged at 3,000×g for ten minutes. The supernatant is discarded, and the precipitate is washed twice in 18% $NA_2SO_4$ solution. The precipitate is again centrifuged, separated from the supernatant, and is dissolved in 0.8 ml of PBS. An equal quantity of 24% $Na_2SO_4$ solution is added and the mixture is centrifuged at 3,000×g for ten minutes. The recovered precipitate is redissolved in 1.0 ml of PBS and is transferred to a dialysis sack and is dialyzed for three days at 4° C. against five changes of PBS. To remove insoluble material, the solution, after dialysis, is centrifuged for ten minutes and the supernatant is recovered for further use. Protein concentration is determined by optical density absorption at 280 nm. Two mg of horseradish peroxidase (Sigma Chemical Co.. type VI, RZ=3.0. specific activity of 300 units per mg) is added to 1 ml of the above antiserum preparation and is mixed at room temperature. The molar ratio of enzyme to antibodies should be about 4:1. The mixture is dialyzed extensively at 4° C. against several changes of PBS. To the final dialysis buffer is added 25% glutaraldehyde to yield a final concentration of 0.2%. This is incubated for 1-2 hours at room temperature and then is dialyzed again at 4° C. against three changes of PBS. The dialysis tube is then transferred to a 50 mM glycine buffer (pH 8.0) and the resulting conjugate is dialyzed against three changes of Tricine buffer (pH 7.5) and subsequently is stored in the same buffer containing 20% fetal calf serum as a stabilizer.

(c) Assay Procedure:

To each of the antibody coated tubes is added 100 $\mu$l of the HRP-conjugated monoclonal antibody (diluted 1:1000, as prepared above). A positive control (inactivated Simian rotavirus to which the monoclonal antibody displays some minor cross reactivity) (available from Kallestad Laboratories) is added in different amounts to the different tubes, as described below. To one tube is added a negative control—lacking the rotavirus—and the tubes are incubated for an hour at room temperature. Each tube is then carefully aspirated and subsequently washed three times with PBS-Tween. 100 $\mu$l of 100 nM Tricine, pH 8.5, is added to each tube, followed by 100 $\mu$l of the luminescent cocktail described above in Example I. After five minutes, the measured light emission is integrated for a thirty second interval, and is related to the amount of virus present. The results are shown in the following table:

| Rotavirus Sample, ul | Light Yield, Arbitrary Units |
| --- | --- |
| 300 | 6,500 |
| 100 | 2,700 |
| 25 | 635 |
| 5 | 69 |
| 1 | 13 |
| Control (0) | 4 |

Inactivated Simian rotavirus is used in this example simply to show the activity of the assay. Human body fluids such as blood serum commonly is tested for the presence of rotavirus rather than for its amount.

EXAMPLE XI

Assay for Thyroxine (a) Preparation of Antibody-coated Tubes:

Antibody-coated transparent polystyrene tubes were prepared in the manner described above in Example X, except that a commercially available rabbit anti-thyroxine antiserum was employed.

(b) HRP - Conjugated Thyroxine:

L-thryoxine (free acid) is reacted with thionyl chloride and methanol. The pH is adjusted to 8.0 using $NaHCO_3$ and the resulting suspension of the thyroxine methyl ester derivative is obtained by filtration. The precipitate is then dissolved in propanol/water/triethylamine (4:1:0.1) and is reacted with an equimolar amount of 1,4-phenylene diisothiocyanate. The resulting precipitate—the thyroxine-monothiourea derivative—was reacted with HRP of the type described in Example X using a five-fold molar excess of the thyroxine derivative over the enzyme, in a solution of 0.5M $Na_2HCO_3$-$Na_2CO_3$ buffer, pH 9.76, for one hour. The resulting conjugate was desalted using a 2.5×25-cm column of Sephadex G-25 equilabrated and developed using Tricine HCl pH 8.5. The protein containing fractions were characterized by UV absorption at 280 nm (for protein concentration) and at 330 nm (for thyroxine content). A typical 330/280 ratio was 0.4 for a successful conjugation. The resulting conjugate was made 20% in fetal calf serum to stabilize the conjugate.

Figure 3:
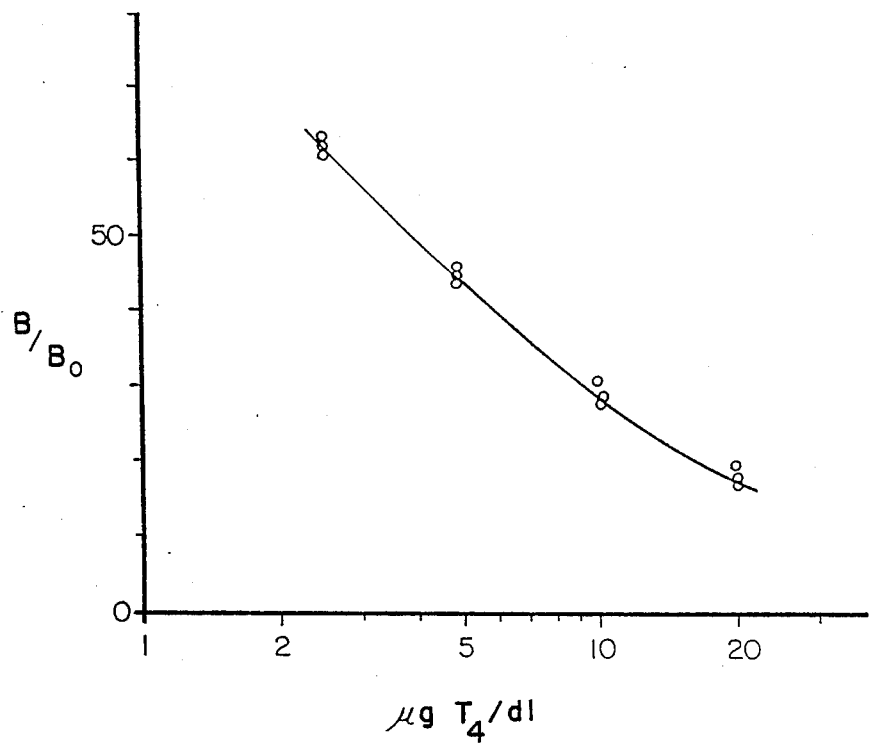
FIG. 3 is a graph in which peroxidase concentration (as measured by luminescence) is plotted against analyte concentration in an exemplary immunoanalysis of $T_4$.

(c) Assay Procedure:

To the antibody-coated tubes was added. 300 $\mu$l of the HRP conjugate (diluted 1:1200 in PBS pH 8.0), and, respectively, 20 $\mu$l of various thyroxine standards set at values of 2.5, 5.0, 10.0 and 20.0 $\mu$g/dl. Following a thirty minute incubation at room temperature, each tube is carefully aspirated and subsequently washed three times with PBS-Tween. Subsequently, 400 $\mu$l of 100 mM Tricine (pH 8.5) was added to each tube. Using a luminometer equipped with an injector, 100 $\mu$l of the luminescent cocktail (Example I) is added to each tube. After a brief incubation, the resulting light emission is integrated over a twenty second interval. A typical standard curve resulting from the above is shown in FIG. 3, in which luminescence (reported as a percentage of that maximally bound in the absence of any competing antigen) is plotted against the concentration of $T_4$. The assay procedure may now be repeated, employing a suitable patient sample in place of the thyroxine standards, the concentration of $T_4$ in the sample being read from the graph of FIG. 3.

Example XII

To each of a series of polystyrene test tubes (12 mm×55 mm were added 100 μl of the horseradish peroxidase-conjugated murine monoclonal antibody to rotavirus (as prepared in Example X, diluted 1:1000), 100 μl of Tricine buffer, pH 8.7, containing varying concentrations of $CaCl_2$, and, last, 300 μl of the luminescent cocktail of Example I. Light output was measured for a period of five seconds after a two minute incubation period, using a Packard Picolite 6500 luminometer. In separate experiments, the background luminescent output of Tricine containing the same varying concentrations was similarly measured, as was the background luminescence of Tricine alone. At levels of $CaCl_2$ between 50–150 mM, a many fold enhancement of peroxidase-mediated light output was observed, with only an insubstantial increase (less than about 2× at this low level) in background light output. At $CaCl_2$ concentration levels of about 175 mM and above, the background luminescence was observed to increase. Thus, one would choose, in this experiment, to utilize $CaCl_2$ in the range of, e.g., 100–175 mM.

While a preferred embodiment of the present invention has been described, it should be understood that various changes, adaptations and modifications may be made therein without departing from the spirit of the invention and the scope of the appended claims.

What I claimed is:

1. A storage-stable reagent useful in luminescence-monitored enzyme assays and which is capable, when reacted with peroxidase, in an alkaline environment, of undergoing a luminescent reaction, the reagent comprising
   (a) a chemiluminescent reagent and an oxidant reactive therewith to cause light emission in a peroxidase-mediated luminescent reaction,
   (b) a sensitivity enhancer capable of increasing the signal-to-background ratio of said luminescent reaction, and
   (c) a pH-regulating composition regulating the pH of the reagent to a value in the range of about 3 to about 6.

2. The reagent of claim 1 in which the chemiluminescent material is a 2,3-dihydro-1,4phthalazinedione and the phenolic sensitivity enhancer is 4-iodophenol or 4-phenylphenol.

3. The reagent of claim 2 in which the oxidant is hydrogen peroxide, perborate ion or urea peroxide.

4. The reagent of claim 1 in which the pH-regulating composition is an acetate or citrate buffer.

5. The reagent of claim 1 in which the pH of the reagent is about 5.0.

6. The reagent of claim 1 including calcium chloride in an amount sufficient to substantially increase peroxidase-mediated luminescence output without significantly increasing background luminescence output.

7. A storage-stable peroxidase-reactive reagent containing
   (a) a 2,3-dihydro-1,4-phthalazinedione and an oxidant reactive therewith to cause light emission in a peroxidase-mediated luminescent reaction in an alkaline environment,
   (b) a phenolic sensitivity enhancer, and
   (c) a pH-regulating composition regulating the pH of the reagent to a value in the range of about 3 to about 6.

8. The reagent of claim 7 wherein the pH-regulating composition regulates the pH of the reagent to about 5.0.

9. An assay kit for performing a peroxidase-mediated, luminescence-monitored assay for an analyte, comprising
   (a) a vessel containing a peroxidase-reactive reagent comprising
      (i) a chemiluminescent 2,3-dihydro-1,4-phthalazinedione and an oxidant reactive therewith to cause light emission in a peroxidase-mediated luminescent reaction in an alkaline environment,
      (ii) a phenolic sensitivity enhancer, and
      (iii) a buffer controlling the pH of the reagent to a value in the range of about 3 to about 6; and
   (b) a separate vessel containing an organic alkaline aqueous buffer capable of adjusting the pH of the first reagent to an alkaline pH favoring light emission.

10. The assay kit of claim 9 in which the organic alkaline aqueous buffer is further characterized by producing negligible buffer-mediated luminescence.

11. The assay kit of claim 10 in which the alkaline buffer is Tricine or glycylglycine.

12. The assay kit of claim 10 in which the peroxidase-reactive reagent includes an acetate or citrate buffer maintaining the pH of that reagent at about 5.0.

13. The kit of claim 9 including, in the peroxidase-reactive reagent, the alkaline buffer or both, $CaCl_2$ in an amount sufficient to substantially increase peroxidase-mediated luminescence output without significantly increasing background luminescence output.

14. The assay kit of claim 9 including a peroxidase conjugate of said analyte or of a binding partner to the analyte.

15. An assay kit for performing a peroxidase-mediated, luminescence-monitored assay for an analyte, comprising
   (a) a vessel containing a peroxidase-reactive reagent including a chemiluminescent composition containing luminol or isoluminol, an oxidant which is hydrogen peroxide, perborate ion or urea peroxide, a sensitivity enhancer which is 4-iodophenol or 4-phenylphenol, and a buffer maintaining the pH of the reagent at a value in the range of about 3–6, and
   (b) a separate vessel containing an organic buffer having a pK in the range of 7.0–9.5 and which includes Tricine or glycylglycine.

16. The kit of claim 15 including, in the alkaline buffer, sufficient $CaCl_2$ to substantially increase peroxidase-mediated luminescence output without significantly increasing background luminescence output.

17. The assay kit of claim 15 including a peroxidase conjugate of the analyte or of a binding partner to the analyte.

18. A method for performing an assay for an analyte in an analyte sample, in which the analyte sample is subjected to a reaction resulting in a peroxidase-containing phase, the quantity of peroxidase in which is related to the quantity of analyte in the sample, the method comprising:
   (a) combining said peroxidase-containing phase with
      (i) a peroxidase-reactive reagent comprising a chemiluminescent 2,3-dihydro-1,4-phthalazinedione, an oxidant reactive therewith to cause light emission in a peroxidase-mediated luminescent reaction in an alkaline environment, a phenolic sensitivity enhancer, and a buffer which maintains the pH of the reagent in the range of about 3 to about 6, and (ii) an organic alkaline aqueous buffer to provide the resulting reaction mixture with an alkaline pH favoring light emission therefrom; and (b) measuring the resulting emitted light.

19. The method of claim 18 in which the anic alkaline buffer is characterized by producing negligible buffer-mediated luminescence.

20. The method of claim 18 in which the peroxidase-reactive reagent is maintained, prior to use, at a pH of about 5.0.

21. The method of claim 18 in which organic alkaline aqueous buffer maintains the pH of the reaction mixture at a value in the range of 7–9.

22. The method of claim 18, in which the organic alkaline aqueous buffer includes Tricine or glycylglycine.

23. The method of claim 18 wherein $CaCl_2$, in sufficient quantity to enhance the peroxidase-mediated luminescence output without significantly increasing background luminescence output, is combined with the chemiluminescent reagent.

24. A method for performing an assay for an analyte in an analyte sample, in which the analyte sample is subjected to a reaction resulting in a peroxidase-containing phase, the quantity of peroxidase in which phase is related to the quantity of analyte in the sample, the method comprising combining the peroxidase-containing phase with (a) a peroxidase-reactive reagent having a pH in the range of 3 to 6, comprising a chemiluminescent reagent and an oxidant reactive therewith to cause light emission in a peroxidase-mediated luminescent reaction in an alkaline environment, and a sensitivity enhancer capable of increasing the signal-to-background ratio of said luminescent reaction, (b) an organic, alkaline buffer to provide the resulting reaction mixture with an alkaline pH favoring light emission, and (c) measuring the resulting emitted light.

25. The method of claim 24 wherein the alkaline buffer is provided with sufficient $CaCl_2$ to enhance the peroxidase-mediated luminescence output without significantly increasing background luminescence output.

* * * * *